United States Patent [19]

Harris et al.

[11] Patent Number: 5,387,426
[45] Date of Patent: Feb. 7, 1995

[54] METHOD OF PREPARING REDUCED FAT FOODS

[75] Inventors: Donald W. Harris; Jeanette A. Little; Keith D. Stanley, all of Decatur, Ill.

[73] Assignee: A.E. Staley Manufacturing Company, Decatur, Ill.

[21] Appl. No.: 968,979

[22] Filed: Oct. 30, 1992

Related U.S. Application Data

[63] Continuation-in-part of Ser. No. 918,862, Jul. 30, 1992, Ser. No. 918,861, Jul. 30, 1992, Ser. No. 918,951, Jul. 30, 1992, Ser. No. 918,952, Jul. 30, 1992, and Ser. No. 908,728, Jul. 6, 1992, which is a continuation of Ser. No. 578,994, Sep. 6, 1990, abandoned, which is a continuation-in-part of Ser. No. 483,208, Feb. 20, 1990, abandoned, said Ser. No. 918,862, and Ser. No. 918,861, each is a continuation-in-part of Ser. No. 746,381, Aug. 16, 1991, abandoned, and Ser. No. 798,291, Nov. 26, 1991, abandoned, said Ser. No. 918,951, is a continuation-in-part of Ser. No. 798,292, Nov. 26, 1991, abandoned, said Ser. No. 918,952, is a continuation-in-part of Ser. No. 746,432, Aug. 16, 1991, abandoned.

[51] Int. Cl.$^6$ .......................... H23L 1/0522
[52] U.S. Cl. ...................... 426/573; 426/18; 426/28; 426/238; 426/578; 426/658; 426/661; 426/603; 426/604; 426/804; 127/29; 127/32; 127/33; 127/36; 127/38; 127/39; 127/40; 127/58; 127/65; 127/67; 127/70; 252/315.3
[58] Field of Search .......... 426/18, 28, 238, 573, 426/578, 658, 661, 603, 604, 804; 127/29, 32, 33, 36, 38, 39, 40, 58, 65, 69-71; 252/315.3

[56] References Cited

U.S. PATENT DOCUMENTS

| | | | |
|---|---|---|---|
| 4,670 | 6/1987 | Chen | 426/573 |
| 675,822 | 6/1901 | Duryea | 127/33 |
| 696,949 | 4/1902 | Duryea | 127/33 |
| 2,068,051 | 1/1937 | Canton | 426/578 |
| 2,131,064 | 9/1938 | Musher | 426/633 |
| 2,503,053 | 4/1950 | Kerr | 127/38 |
| 2,791,508 | 5/1957 | Rivoche | 426/573 |
| 2,805,995 | 9/1957 | Adelson | 252/33.6 |
| 2,978,446 | 4/1961 | Battista et al. | 260/212 |
| 3,023,104 | 2/1962 | Battista | 99/1 |
| 3,067,067 | 12/1962 | Etheridge et al. | 127/74 |
| 3,093,486 | 6/1963 | Krett | 99/144 |
| 3,133,836 | 5/1964 | Winfrey | 127/71 |
| 3,197,337 | 7/1965 | Schink | 127/28 |
| 3,219,483 | 11/1965 | Goos | 127/28 |
| 3,351,489 | 11/1967 | Battista | 127/32 |
| 3,532,602 | 10/1970 | Seidman | 195/31 |
| 3,556,942 | 1/1971 | Hathaway | 195/31 |
| 3,582,359 | 6/1971 | Horn | 426/573 |
| 3,586,536 | 6/1971 | Germino | 127/32 |
| 3,600,186 | 8/1971 | Mattson | 99/1 |
| 3,632,475 | 1/1972 | Sugimoto et al. | 127/71 |
| 3,666,557 | 5/1972 | Jensen | 127/32 |
| 3,671,269 | 6/1972 | Germino | 99/139 |
| 3,705,811 | 12/1972 | Yoshida | 99/91 |
| 3,717,475 | 2/1973 | Germino | 99/134 |
| 3,730,840 | 5/1973 | Sugimoto et al. | 195/31 |
| 3,830,697 | 8/1974 | Yoshida | 195/31 R |
| 3,879,212 | 4/1975 | Yoshida | 106/213 |
| 3,881,991 | 5/1975 | Kurimoto et al. | 195/31 |
| 3,883,365 | 5/1975 | Forsberg | 127/60 |
| 3,928,062 | 12/1975 | Yamauchi | 127/60 |

(List continued on next page.)

FOREIGN PATENT DOCUMENTS 1016006 8/1977 Canada.

(List continued on next page.)

OTHER PUBLICATIONS

Allmere et al., Derwent Abstracts, 93-174080, for SU 1736975, May 1992.

(List continued on next page.)

*Primary Examiner*—Joseph Golian
*Attorney, Agent, or Firm*—Arnold, White & Durkee

[57] ABSTRACT

A method of preparing reduced fat foods is provided which employs a retrograded, hydrolyzed, heat-treated, and fragmented, amylose starch. Amylose is precipitated and hydrolyzed with acid or α-amylase, solubles are removed by a heat treatment and the resulting solids are then fragmented to form an aqueous dispersion that is useful in replacing fat in a variety of food formulations. The amylose can be derived from a native starch which contains amylose, e.g. common corn starch and high amylose corn starch, by gelatinizing the starch followed by precipitation of the amylose.

21 Claims, No Drawings

U.S. PATENT DOCUMENTS

| | | | |
|---|---|---|---|
| 3,962,465 | 6/1976 | Richter et al. | 127/48 |
| 3,986,890 | 10/1976 | Richter et al. | 127/38 |
| 4,009,291 | 2/1977 | Mitchell | 426/548 |
| 4,069,157 | 1/1978 | Hoover | 210/433 M |
| 4,143,163 | 3/1979 | Hutchison | 426/96 |
| 4,143,174 | 3/1979 | Shah | 426/570 |
| 4,192,900 | 3/1980 | Cheng | 426/578 |
| 4,199,374 | 4/1980 | Dwivedi | 127/60 |
| 4,209,503 | 6/1980 | Shah | 424/49 |
| 4,263,334 | 4/1981 | McGinley | 426/573 |
| 4,276,312 | 6/1981 | merritt | 426/96 |
| 4,291,065 | 9/1981 | Zobel | 426/549 |
| 4,305,964 | 12/1981 | Moran | 426/99 |
| 4,308,294 | 12/1981 | Rispoli | 426/564 |
| 4,423,084 | 12/1982 | Trainor | 426/589 |
| 4,477,480 | 10/1984 | Seidel | 426/578 |
| 4,492,714 | 1/1985 | Cooper | 426/602 |
| 4,510,166 | 4/1985 | Lenchin et al. | 426/565 |
| 4,533,254 | 8/1985 | Cook et al. | |
| 4,536,408 | 8/1985 | Morehouse et al. | 426/250 |
| 4,551,177 | 11/1985 | Trabiano | 106/210 |
| 4,560,559 | 12/1985 | Ottenberg | 426/19 |
| 4,587,131 | 5/1986 | Bodor | 426/603 |
| 4,591,507 | 5/1986 | Bodor | 426/604 |
| 4,643,773 | 2/1987 | Day | 127/30 |
| 4,726,957 | 2/1988 | Lacourse | 426/578 |
| 4,728,526 | 3/1988 | Avera | 426/633 |
| 4,744,987 | 5/1988 | Hutchison et al. | 424/156 |
| 4,761,292 | 8/1988 | Augustine | 426/321 |
| 4,787,939 | 11/1989 | Barker | 127/37 |
| 4,810,307 | 3/1989 | Caton | 127/63 |
| 4,810,646 | 3/1989 | Jamas | 435/101 |
| 4,814,195 | 3/1989 | Yokohama | 426/633 |
| 4,828,868 | 5/1989 | Lasdon | 426/633 |
| 4,832,977 | 5/1989 | Avera | 426/633 |
| 4,859,484 | 8/1989 | Bielskis | 426/96 |
| 4,869,919 | 9/1989 | Lowery | 426/604 |
| 4,885,180 | 12/1989 | Cochran | 426/241 |
| 4,886,678 | 12/1989 | Chiu | 426/578 |
| 4,911,946 | 3/1990 | Singer | 426/658 |
| 4,917,915 | 4/1990 | Cain | 426/573 |
| 4,937,091 | 6/1990 | Zallie | 426/582 |
| 4,942,055 | 7/1990 | Avera | 426/633 |
| 4,948,615 | 8/1990 | Zallie | 426/573 |
| 4,954,178 | 9/1990 | Caton | 127/32 |
| 4,957,750 | 9/1990 | Cochran | 426/19 |
| 4,962,094 | 10/1990 | Jamas | 514/54 |
| 4,971,723 | 11/1990 | Chiou | 252/315.3 |
| 4,981,709 | 1/1991 | Furcsik | 426/565 |
| 4,988,531 | 1/1991 | Moore | 426/578 |
| 4,990,335 | 2/1991 | Gupta | 426/602 |
| 5,034,240 | 7/1991 | Tanaka | 426/607 |
| 5,035,904 | 7/1991 | Huang | 426/243 |
| 5,037,929 | 8/1991 | Rajagopalan | 426/578 |
| 5,051,271 | 9/1991 | Iyengar et al. | 426/658 |
| 5,094,872 | 3/1992 | Furcsik | 426/578 |
| 5,104,674 | 4/1992 | Chen | 426/573 |
| 5,106,644 | 4/1992 | El-Nokaly | 426/603 |
| 5,110,612 | 5/1992 | Quarles | 426/573 |
| 5,131,953 | 7/1992 | Kasoca et al. | 127/65 |
| 5,137,742 | 8/1992 | Bakal | 426/589 |
| 5,147,665 | 9/1992 | Furcsik | 426/19 |
| 5,192,569 | 3/1993 | McGinley et al. | 426/96 |

FOREIGN PATENT DOCUMENTS

| | | |
|---|---|---|
| 0052899 | 2/1982 | European Pat. Off. |
| 0237120 | 9/1987 | European Pat. Off. |
| 0298561 | 1/1989 | European Pat. Off. |
| 0327120 | 8/1989 | European Pat. Off. |
| 0327288 | 8/1989 | European Pat. Off. |
| 0340035 | 11/1989 | European Pat. Off. |
| 0367064 | 5/1990 | European Pat. Off. |
| 372184 | 6/1990 | European Pat. Off. |
| 0387940 | 9/1990 | European Pat. Off. |
| 0420314 | 4/1991 | European Pat. Off. |
| 0420315 | 4/1991 | European Pat. Off. |
| 0427312 | 5/1991 | European Pat. Off. |
| 0430329 | 6/1991 | European Pat. Off. |
| 443844 | 8/1991 | European Pat. Off. |
| 0470870 | 2/1992 | European Pat. Off. |
| 480443 | 4/1992 | European Pat. Off. |
| 0486936 | 5/1992 | European Pat. Off. |
| 142646A | 7/1980 | German Dem. Rep. |
| 161178A | 5/1985 | German Dem. Rep. |
| 110957 | of 1897 | Germany |
| 60160833 | 8/1985 | Japan |
| 3-296501 | 12/1991 | Japan |
| 4-46901 | 2/1992 | Japan |
| 2247242 | 2/1992 | United Kingdom |
| WO87/04465 | 7/1987 | WIPO |
| WO89/12403 | 12/1989 | WIPO |
| WO90/00010 | 1/1990 | WIPO |
| WO90/06343 | 6/1990 | WIPO |
| WO90/15147 | 12/1990 | WIPO |

(List continued on next page.)

"Low fat ground beef patties", brochure, A. E. Staley Mfg. Co. (Oct. 1991).

(List continued on next page.)

FOREIGN PATENT DOCUMENTS

WO91/01091 2/1991 WIPO.
WO91/01092 2/1991 WIPO.
WO91/07106 5/1991 WIPO.
WO91/12728 9/1991 WIPO.
WO92/02614 2/1992 WIPO.
WO92/21703 12/1992 WIPO.

OTHER PUBLICATIONS

"Low-fat pork sausage patty", formula sheet CFSF7 196211, A. E. Staley Mfg. Co.
"New generation of foods with reduced fat", Food Enigineering, pp. 23–26 (Jan. 1990).
"RANNIE High Pressure Laboratory Homogenizer", service manual, Rannie a/s, Roholmsvej 8, DK-2620, Denmark (1988).
"Staley Formulation of Food Starch-Modified", new product review presented to U.S. Food and Drug Administration by A. E. Staley Mfg. Co. (Nov. 1990).
"STELLAR Fat Replacer, Structure", technical information bulletin, A. E. Staley Mfg. Co., TIB 29 195060 (Jun. 1991).
Atwell et al, "Characterization of quinoa starch", Cereal Chemistry, vol. 60, pp. 9–11 (1983).
BeMiller, "Gums", Encyclopedia of Food Science & Technology, vol. 2, pp. 1338–1344 (John Wiley & Sons 1992).
Bouchard et al, "High performance liquid chromatographic monitoring of carbohydrate fractions in partially hydrolyzed corn starch", J. Agric. Food Chem., vol. 36, pp. 1188–1192 (1988).
Dickinson, "Particle gels", Chemistry & Industry, pp. 595–599 (Oct. 1990).
Duxbury, "Modified food starches partially replace fats, oils & provide smooth texture", Food Processing, pp. 86–88 (Nov. 1990).
Duxbury, "Fat-sparing starch can replace 100% fat/oil for 96% calorie reduction", Food Processing, p. 38 (Dec. 1990).
Dziezak, "Membrane separation technology offers processors unlimited potential", Food Technology, pp. 108–113 (Sep. 1990).
Faulkner et al, "Size reduction", Encyclopedia of Chemical Technology, vol. 21, pp. 132–162 (Kirk Othmer eds., John Wiley & Sons, 1983).
Ghiasi et al, "Effects of flour components and dough ingredients on starch gelatinization", Cereal Chemistry, vol. 60, No. 1, pp. 58–61 (1983).

Giese, "Developing low-fat meat products", Food Technology, pp. 100–108 (Apr. 1992).
Jane et al, "Structure studies of amylose-V complexes and retrograded amylose by action of alpha Amylases, and a new method for preparing amylodextrins", Carbohydrate Research, vol. 132, pp. 105–118 (1984).
Kerr, Chemistry and Industry of Starch, 2d ed., pp. 564–567 (Acdemic Press 1950).
Knightly, "The evolution of softners and conditioners used in baked foods", The Bakers Digest, pp. 64–75 (Oct. 1973).
Lansky et al, "Properties of the fractions and linear subfractions from various starches", vol. 71, pp. 4066–4075 (1949).
Luu et al, "Model structure for liquid water, etc.", Travaux de la Societe de Pharmacie de Montpellier, vol. 41, No. 3, pp. 203–212 (1981) (Translation Attached).
Manley, Technology of Biscuits, Crackers and Cookies, pp. 335–347 (Ellis Horwood 1983).
Mason, "Chemistry with ultrasound", Critical Reports on Applied Chemistry, vol. 28, pp. 1–26, 91–98, 159–187 (Elsevier Science Publishers 1990).
Matthews, Legumes: Chemistry, Technology, and Human Nutrition, pp. 226–229 (Marcel Dekker 1989).
Matz, Cookie and Cracker Technology, pp. 163–167 (AVI Publishing 1968).
Mussleman et al, "Electron microscopy of unmodified and acid-modified corn starches", Cereal Chemistry, vol. 45, pp. 162–171 (1968).
Nara et al, "Study on relative crystallinity of moist potato starch", Starke/Starch, vol. 30, pp. 111–114 (1978).
Orr, "Size measurement of particles", Encyclopedia of Chemical Technology, vol. 21, pp. 106–131 (Kirk Othmer eds., John Wiley & Sons, 1983).
Pancoast et al, Handbook of Sugars, pp. 157–287 (AVI Publishing 1980).
Patterson, Hydrogenation of Fats and Oils, pp. 44–48, 173–182, 291–304 (Applied Science Publishers, 1983).
Pszczola, "Oat-bran-based ingredient blend replaces fat in ground beef and pork sausage", Food Technology, pp. 60–66 (Nov. 1991).
Reuther et al, "Structure of maltodextrin gels-a small angle X-ray scattering study", Colloid and Polymer Science, vol. 261, pp. 271–276 (1983).
Richards, BNreads, Rolls and Sweet Doughs, pp. 92–95 (Peacock Business Press, 1973).

OTHER PUBLICATIONS

Richardson, "Molecular mobilities of instant starch gels determined by oxygen–17 and carbon–14 nuclear magnetic resonance", Journal of Food Science, vol. 53, pp. 1175–1180 (1988).

Russell et al, "Characterization of resistant starch from wheat and maize", Journal of Cereal Science, vol. 9, pp. 1–15 (1989).

Savage et al, "Effects of certain sugars alcohols on the swelling of cornstarch granules", Cereal Chemistry, vol, 55, No. 4, pp. 447–454 (1978).

Spies et al, "Effect of sugars on starch gelatinization", Ceral Chemistry, vol. 59, No. 2, pp. 128–131 (1982).

Stadelman et al, Egg and Poultry Meat Processing, pp. 52–63 (Ellis Horwood 1988).

Swientek, "'Microfluidizing' technology enhances emulsion stability", Food Processing, pp. 152–153 (Jun. 1990).

Taki, "Functional ingredient blend produces low–fat meat products to meet consumer expectations", Food Technology, pp. 70–74 (Nov. 1991).

Teot, "Resins water–soluble", Encyclopedia of Chemical Technology, vol. 20, pp. 207–230 (John Wiley & Sons 1982).

Trout, "Pasteurization", Encyclopedia of Food Science, pp. 600–604 (Peterson et al eds., AVI Publ. Co., 1978).

Wang, "Meat processing I", Encyclopedia of Food Engineering, pp 545–557 (AVI Publishing 1986).

Whistler et al, "Effect of acid hydrolisis on the retrogradation of amylose", Cereal Chemistry, vol. 25, No. 6, pp. 418–424 (1948).

White et al, "Predicting gelatinization temperatures of starch/sweetener systems for cake formulations by differential scanning calorimetry. I. Development of model." Cereal Foods World, vol. 35, No. 8, pp. 728–731 (Aug. 1990).

Wilhoft, "Recent developments on the bread staling problem", The Bakers Digest, pp. 14–20 (Dec. 1973).

Yamaguchi et al, "Electron microscopic observations of waxy maize starch", Journal of Ultrastructure Research, vol. 69, pp. 249–261 (1979).

Paselli SA2; "The Natural Alternative to Fats and Oils" (Avebe b.a., Foxhol, Holland, Ref. No. 05.12.31.167 EF).

R. L. Whistler, et al., *Starch: Chemistry and Technology*, pp. 25–35 (Academic Press, Inc., New York, N.Y., 1984).

A. C. Lavanchy and F. W. Keith, "Centrifugal Separation", *Encyclopedia of Chemical Technology*, vol. 5, pp. 194–223 (Kirk–Othmers, ed. 5, John Lilard Sons, Inc. New York, N.Y., 3d ed. 1979).

D. R. Paul and C. Morel, "Membrane Technology", *Encyclopedia of Chemical Technology*, vol. 15, pp. 92–131 (Kirk–Othmer, eds., John Wiley & sons, Inc., New York, N.Y., 3d ed., 1981).

P. R. Klinkowski, "Ultrafiltration", *Encyclopedia of Chemical Technology*, vol. 23, pp. 439–461 (Kirk–Othmer, eds., John Wiley & Sons, Inc., New York, N.Y., 3d ed., 1983).

"Solve Tough Process Filtration Problems with Ceraflo Ceramic Systems", a technical bulletin, Lit. No. SD113, 2/89 89–418, published (1989) by Millipore Corporation, Bedford, Mass.

H. Reuter, "Homogenization", *Encyclopedia of Food Science*, pp. 374–376, (M. S. Peterson and A. H. Johnson, eds., AVI Publ. Co., Westport, Conn., 1978).

L. H. Rees and W. D. Pandolfe, "Homogenizers", *Encyclopedia of Food Engineering*, pp. 467–472 (C. W. Hall, et al., eds., AVI Publ. Co., Westport, Conn., 1986).

W. C. Griffin, "Emulsions", *Encyclopedia of Chemical Technology*, vol. 8, pp. 900–930 (Kirk–Othmer eds., John Wiley & Sons, Inc., New York, N.Y., 3d ed., 1979).

R. L. Whistler, et al., *Starch: Chemistry and Technology*, pp. 25–35 (Academic Press, Inc., New York, N.Y., 1984).

T. H. Applewhite, "Fats and Fatty Oils", *Encyclopedia of Chemical Technology*, vol. 9, pp. 795–831 (Kirk–Othmer, eds., John Wiley & Sons, Inc., New York, N.Y., 3d ed., 1980).

Food Labelling; Serving Sizes, 55 Fed. Reg. 29517 (1990) (to be codified at 21 C.F.R. 101.12).

Food Labelling; Definitions of the Terms Cholesterol Free, Low Cholesterol and Reduced Cholesterol, 55 Fed. Reg. 29456 (1990).

K. Koizumi, et al., "High–Performance Anion–Exchange Chromatography of Homogeneous D–Gluco–Oligosaccharides and –Polysaccharides (Polymerization Degree equal to or greater than 50) With Pulsed Amperometric Detection", *Journal of Chromatography*, 46, pp. 365–373 (1989).

OTHER PUBLICATIONS

P. A. Schweitzer, *Handbook of Separation Techniques for Chemical Engineers*, pp. 4–60 to 4–88 (McGraw Hill, New York, N.Y., 1988).

R. Shute, "Hydrothermal Modification of Starches: The Differences between Annealing and Heat/Moisture–Treatment", *Starch/Staerke*, vol. 44, pp. 205–214 (1992).

International Search Report in PCT/US/06646.

D. Sievert et al., "Enzyme–Resistant Starch. I. Characterization and Evaluation by Enzymatic, Thermoanalytical, and Microscopic Methods", *Cereal Chemistry*, vol. 66, pp. 342–347 (1989).

O. A. Battista et al., "Colloidal Macromolecular Phenomena. Part II. Novel Microcrystals of Polymers", *Journal of Applied Polymer Science*, vol. 11, pp. 481–498 (1967).

N. Z. Erdi et al., "Rheological Characteristics of Polymeric Micro–crystal Gels", *Journal of Colloid and Interface Science*, vol. 28, pp. 36–47.

"Nepol Amylose", Market Development Bulletin No. 101, A. E. Staley Mfg. Company (1962).

U.S. Ser. No. 07/918,952, filed Jul. 30, 1992.
U.S. Ser. No. 07/918,862, filed Jul. 30, 1992.
U.S. Ser. No. 07/746,381, filed Aug. 16, 1991.
U.S. Ser. No. 07/798,291, filed Nov. 26, 1991.
U.S. Ser. No. 07/918,861, filed Jul. 30, 1992.
U.S. Ser. No. 07/918,951, filed Jul. 30, 1992.
U.S. Ser. No. 07/798,292, filed Nov. 26, 1991.

I. Larsson and A. Eliasson, "Annealing of Starch at an Intermediate Water Content", *Starch*, vol. 43, No. 6, pp. 227–231 (Jun. 1991).

U.S. Ser. Nos. 483,208, filed Feb. 20, 1990, and 578,994, filed Sep. 6, 1990.

"STELLAR Fat Replacer", a technical data sheet, published by A. E. Staley Manufacturing Company, TDS 513 192250.

"STELLAR Fat Replacer; Handling, Storage and Preparation", a technical information bulletin, published by A. E. Staley Manufacturing Company, TIB 28 195060.

J. Jane et al., "Preparation and Properties of Small–Particle Corn Starch", *Cereal Chemistry*, vol. 69, pp. 280–283 (1992).

A. H. Young, "Evaluation of Microcrystals Prepared from MIRA–QUIK C in the Pilot Plant Spray Dried in the Presence of Sodium Carboxymethylcellulose (C9–112)", Project Report No. RD 73–17 of A. E. Staley Manufacturing Company.

"C9–112 Microcrystalline Starch", a product bulletin of A. E. Staley Manufacturing Company, Decatur, Ill.

D. Duxbury, "Pre–Hydrated Gums Eliminate Lumping, Long Hydration Times", *Food Processing* (Jun. 1992).

M. Falkiewicz, "Avicel in Suspensions–Dispersion, Rheology and Colloid Science", *Soap, Cosmetics, Chemical Specialties*, pp. 27–34 (Apr. 1979).

U.S. Ser. No. 07/746,432, filed Aug. 16, 1991.

O. A. Battista et al., "Microcrystalline Cellulose", *Industrial and Engineering Chemistry*, vol. 54, pp. 20–29 (1962).

"Avicel RC 581 Technical Bulletin", Bulletin No. RC-11 of FMC Corporation, Marcus Hook, Pa., 11/69–1M.

"Avicel Microcrystalline Cellulose; the Non–caloric Ingredient" a bulletin of American Viscose Corporation, Marcus Hook, Pa. (later a division of FMC Corporation).

"Avicel RC–591 in Foods", Bulletin No. RC–22, FMC Corporation, Marcus Hook, Pa. (May 1972).

"Avicel RC in Bakery Products", Bulletin No. RC–35, FMC Corporation, Marcus Hook, Pa.

"Avicel RC in Canned Foods", Bulletin No. RC–31, FMC Corporation, Marcus Hook, Pa. (May 1972).

"Avicel Pricing", a bulletin apparently of American Viscose Corporation, Marcus Hook, Pa. (later a division of FMC Corporation).

O. B. Wurzburg, *Modified Starches: Properties and Uses*, pp. 18–23, 38–40, 244–245, and 251–252 (CRC Press, Inc., Boca Raton, Fla., 1986).

G. R. Sanderson, "Polysaccharides in Foods", *Food Technology*, pp. 50–57 and 83 (Jul. 1981).

"Gums and Starches Bulk Up Low–Cal Foods", *Food Engineering*, (Jan. 1990).

"STA–SLIM starches", a technical data sheet published by A. E. Staley Manufacturing Company, Decatur, Ill.

"Reduced–Oil Salad Dressings", a technical publications of the A. E. Staley Manufacturing Company, Decatur, Ill.

N. Krog, "Functions of Emulsifiers in Food Systems", *J. Am. Oil Chemists' Society*, vol. 54, pp. 124–131 (1977).

J. D. Dziezak, "Emulsifiers: The Interfacial Key to Emulsion Stability", *Food Technology*, vol. 42, No. 10, pp. 171'186.

METHOD OF PREPARING REDUCED FAT FOODS

CROSS-REFERENCE TO RELATED APPLICATIONS

This application is a continuation-in-part of U.S. application Ser. No. 07/918,862, filed Jul. 30, 1992 (which is a continuation-in-part of Ser. No. 07/746,381, filed Aug. 16, 1991, now abandoned, and Ser. No. 07/798,291, filed Nov. 26, 1991, now abandoned); U.S. application Ser. No. 07/918,861, filed Jul. 30, 1992 (which is a continuation-in-part of Ser. No. 7/746,381, now abandoned, filed Aug. 16, 1991, now abandoned and 07/798,291, filed Nov. 26, 1991, now abandoned); U.S. application Ser. No. 07/918,951 filed Jul. 30, 1992 (which is a continuation-in-part of Ser. No. 07/798,292, filed Nov. 26, 1991, now abandoned); and U.S. application Ser. No. 07/918,952, filed Jul. 30, 1992 (which is a continuation-in-part of Ser. No. 07/746,432, filed Aug. 16, 1991, now abandoned), the disclosures of all of which are incorporated herein by reference. This application is also a continuation-in-part of U.S. application Ser. No. 07/908,728, filed Jul. 6, 1992, which was a continuation of U.S. application Ser. No. 07/578,994, filed Sep. 6, 1990, now abandoned, which was a continuation-in-part of U.S. application Ser. No. 07/483,208, filed Feb. 20, 1990, now abandoned.

FIELD OF THE INVENTION

This invention relates to food formulations in which at least a portion of the fat and/or oil is replaced by a carbohydrate.

BACKGROUND OF THE INVENTION

Lenchin et al. U.S. Pat. No. 4,510,166 discloses converted starches having a DE less than 5 and certain paste and gel characteristics which are used as a fat and/or oil replacement in various foods, including ice cream and mayonnaise. The converted starches are described as dextrins, acid-converted starches (fluidity starches), enzyme-converted starches and oxidized starches. It is also disclosed that if the converted starches are not rendered cold-water soluble by the conversion, they are pregelatinized prior to use or cooked during use.

A product bulletin entitled "Paselli SA2; The Natural Alternative to Fats and Oils" (AVEBE b.a., Foxhol, Holland, Ref. No. 05.12.31.167 EF) discloses the use of a low-DE-hydrolysate (DE less than 3) made from potato starch as a replacement for fifty percent of the fat with an amount of the low-DE-potato starch hydrolysate plus water (starch hydrolysate at 28% dry solids) equal to the amount of fat replaced.

Richter et al. U.S. Pat. Nos. 3,962,465 and 3,986,890 disclose the use of thermoreversible gels of a starch hydrolysate (formed by enzymatic hydrolysis) as a substitute for fat in a variety of foods, including cake creams and fillings, mayonnaise and remoulades, cream cheeses and other cheese preparations, bread spreads, pastes, meat and sausage products, and whipped cream.

Chiu U.S. Pat. No. 4,971,723 discloses partially debranched starch prepared by enzymatic hydrolysis of the α-1,6-D-glucosidic bonds of the starch, comprising amylopectin, partially debranched amylopectin and up to 80% by weight, short chain amylose and that the partially debranched starch is useful in a variety of ways depending upon the degree of debranching. It is disclosed that a waxy maize starch (or other waxy starch) can be partially debranched (i.e. to 25% to 70% short chain amylose) to yield sufficient short chain amylose to form a thermally reversible gel in an aqueous starch suspension. It is further disclosed that the same degree of debranching of waxy starches is preferred for lending a fat-like, lubricating texture to an aqueous starch dispersion.

PCT Publication No. WO 91/07106, published May 30, 1991, discloses a method of preparing a food grade, insoluble bulking agent from starch that is also disclosed to be useful as a bulking or texturizing agent in low-fat food formulations. The method of preparing the starch comprises a retrogradation process followed by enzymatic (e.g., α-amylase) or chemical (e.g., acid) hydrolysis of amorphous regions in the retrograded product. In this process, amylose is allowed to retrograde from a solution of gelatinized starch. The hydrolysis is then undertaken to reduce or eliminate amorphous regions in the retrograded product.

SUMMARY OF THE INVENTION

In one aspect, this invention relates to a method of preparing a heat-treated and fragmented amylose starch hydrolysate comprising:

gelatinizing and retrograding an amylose starch in the presence of an aqueous medium to prepare an aqueous slurry of retrograded amylose;

hydrolyzing said retrograded amylose to a degree sufficient to permit physical fragmentation to form a particle gel comprised of a minor amount of said retrograded amylose in a major amount of an aqueous medium;

physically separating said hydrolyzed and retrograded amylose from an aqueous medium at an elevated temperature to remove a water-soluble hydrolysate fraction with said aqueous medium to produce a hydrolyzed and retrograded amylose free of water-soluble hydrolysate products;

physically fragmenting a minor amount of said hydrolyzed and retrograded amylose essentially free of water-soluble hydrolysate products in a major amount of an aqueous medium to produce a particle gel thereof.

In another aspect, this invention relates to a food formulation having a reduced level of fat and/or oil comprising a mixture of a foodstuff and a particle gel as a replacement for at least a substantial portion of the fat and/or oil of said foodstuff, said particle gel comprising a minor amount of a retrograded, hydrolyzed, heat-treated, and fragmented, amylose starch and a major amount of an aqueous liquid.

In another aspect, this invention relates to a method of formulating a food containing a fat and/or oil ingredient comprising replacing at least a substantial portion of said fat and/or oil ingredient with a particle gel as a replacement for at least a substantial portion of the fat and/or oil of said foodstuff, said particle gel comprising a minor amount of a retrograded, hydrolyzed, heat-treated, and fragmented, amylose starch and a major amount of an aqueous liquid.

By "retrograded, hydrolyzed, heat-treated, and fragmented, amylose starch" is meant a starch material comprised of amylose which has been subjected to gelatinization and retrogradation of the amylose followed by hydrolysis and heat-treatment (in the presence of water) to solubilize and remove water-soluble hydrolysate materials and then physically fragmented. The hydrolysis and fragmentation will be sufficient to produce a hydrolysate which will form an aqueous dispersion having the characteristics of a particle gel. The retrograded, hydrolyzed, heat-treated and fragmented amylose starch will preferably have only a minor amount (e.g. less than about 25%, preferably less than 10% and more preferably less than about 5% by weight on a dry solids basis) of hot-water solubles (e.g. the amount of solubles at 90° C.). The amount of hot-water solubles can be determined as in PCT Publication No. WO 91/12728, published Sep. 5, 1991, at pages 55 and 56, but with the use of water maintained at an elevated temperature (e.g. 90° C.).

In another aspect, this invention relates to an aqueous dispersion useful as a replacement for fats and/or oils comprising a major amount by weight of water and a minor amount by weight of a retrograded, hydrolyzed, heat-treated, and fragmented amylose starch, the degree of hydrolysis and fragmentation of said starch being sufficient to form a particle gel of said dispersion.

The terms "foodstuff" and "food", as used herein, are intended to broadly cover nutritional and/or functional materials that are ingested by humans in the course of consuming edible fare. The term "fats and/or oils" is intended to broadly cover edible lipids in general, specifically the fatty acid triglycerides commonly found in foods. The terms thus include solid fats, plastic shortenings, fluid oils (and fully or partially hydrogenated oils), and the like. Common fatty acid triglycerides include cottonseed oil, soybean oil, corn oil, peanut oil, canola oil, sesame oil, palm oil, palm kernel oil, menhaden oil, whale oil, lard, and tallow. The technology of fats and/or oils is described generally by T. H. Applewhite, "Fats and Fatty Oils", *Encyclopedia of Chemical Technology*, Vol. 9, pp. 795–831 (Kirk-Othmer, eds., John Wiley & Sons, Inc., New York, N.Y., 3d ed., 1980), the disclosure of which is incorporated by reference.

The use of the terms "major" and "minor" in context together in this specification is meant to imply that the major component is present in a greater amount by weight than the minor component, and no more nor less should be inferred therefrom unless expressly noted otherwise in context.

DETAILED DESCRIPTION OF THE INVENTION

The retrograded, hydrolyzed, heat-treated, and fragmented amylose starch is made by the sequential steps of gelatinization, retrogradation, hydrolysis, heat treatment, and fragmentation of a starch material containing amylose. Starch is generally comprised of a highly-branched glucan having $\alpha$-1,4 and $\alpha$-1,6 linkages, denominated amylopectin, and a substantially linear glucan, having almost exclusively $\alpha$-1,4 linkages, denominated amylose. Methods of determining the amounts of each are referenced in R. L. Whistler et al., *Starch: Chemistry and Technology*, pp. 25–35 (Academic Press, Inc., New York, N.Y., 1984), the disclosure of which is incorporated by reference. As used herein, the term "amylose" includes native amylose and, unless otherwise expressly noted in context, modified amylose. Examples of modified amylose include acid-modified amylose, enzyme-modified amylose (e.g. $\alpha$-amylase, $\beta$-amylase, isoamylase, or pullulanase) and chemically substituted amylose, provided the levels of chemical substitution (e.g. hydroxypropylation, crosslinking, etc. ) are insufficient to prevent precipitation and enzymatic hydrolysis of the amylose to the desired degree. Starches having a substantial proportion (i.e. at least 15% by weight) of amylose are preferred and examples of these include the common non-mutant starches of cereals, tubers and legumes, e.g. corn, wheat, rice, potato, tapioca, and pea. Preferred for use herein are starches derived from corn (Zea mays) such as common corn starch and high amylose corn starch, each of which are examples of starches containing greater than 15% amylose. Examples of such starches from high amylose corn include HI-SET® C and HYLON™ (each about 55% amylose by weight) and HYLON™ VII (about 70% amylose by weight), all available from National Starch and Chemical Corporation, Bridgewater, N.J.

In certain embodiments, the starch is comprised of a major amount of amylose. In such embodiments, the starch employed is from a mutant variety of native starch which contains a major amount of amylose or is obtained by fractionation of amylose from a starch variety containing both amylose and amylopectin. Methods for the fractionation of amylose and amylopectin from native starch are disclosed in, for example, Etheridge U.S. Pat. No. 3,067,067.

If the starch chosen as a starting material is not in pre-gelatinized or instant form, the starch must be gelatinized or pasted prior to precipitation of the amylose. The gelatinization or pasting process disrupts, at least in substantial part, the associative bonding of the starch molecules in the starch granule. This permits the amylose to associate and precipitate. This disruption is accomplished by heating a slurry of the starch to a sufficient temperature for a sufficient length of time depending upon the inherent resistance of the particular starch to gelatinization and the amount of moisture present in the slurry. The slurry will typically be comprised of a major amount of water (i.e. at least 50% by weight) and a minor amount of the starch starting material (i.e. less than about 50% by weight). Preferably, the starch slurry will contain at least about 5% starch, typically between about 7% to about 10% starch. The pH of the slurry will generally be substantially neutral, i.e. from about 3.5 to about 9 and more preferably from about 6 to 8, to minimize hydrolysis of the starch molecules. The time, temperature, slurry solids, and pH should be optimized to gelatinize the starch, yet minimize hydrolysis of the starch.

The appropriate temperature, pressure and period of treatment needed to provide a starch paste is preferably obtained by processing aqueous starch slurries in equipment commonly known in the art as steam injection heaters or jet cookers. In such equipment, superatmospheric steam is injected and mixed with a water slurry of starch in a throat section of a jet. Upon contact with the injected steam, the starch granules are uniformly and thermally treated under turbulent conditions whereupon the starch granules are gelatinized and solubilized. Examples of steam injection heaters wherein the temperature, pressure and feed rate can be regulated to provide the desired starch pastes are disclosed in U.S. Pat. Nos. 3,197,337; 3,219,483; and 3,133,836. More uniformly solubilized starch pastes are obtained by use of the steam injection heater in combination with a holding zone such as coiled tubing or a pressurized tank constructed to minimize liquid channeling. Other pasting equipment, e.g. heat exchangers, homogenizers, cookers, votators, sizeometer cookers, kettle cookers, etc., may be employed provided the pasting conditions can be adequately maintained.

The starch solution may also be treated to remove impurities therefrom. Treatment with, for example, activated carbon will remove residual proteins and lipids that may contribute to off-flavors and/or colors.

The gelatinized starch is then optionally treated with a debranching enzyme, i.e. an enzyme capable of hydrolyzing the 1,6-glucosidic bond of amylopectin without significant capability of hydrolyzing the 1,4-glucosidic bond. Enzymes from a variety of sources are capable of debranching amylopectin. U.S. Pat. No. 3,370,840 (Sugimoto et al.) describes sources of debranching enzymes, the disclosure of which is incorporated herein by reference. Examples of useful enzymes include pullulanases derived from bacteria of the genus Aerobacter (e.g. E.C. 3.2.1.41 pullulan 6-glucanohydrolase) and isoamylases derived from bacteria of the genus Pseudomonas (e.g. E.C. 3.2.1.68 glycogen 6-glucanohydrolase). Particularly useful enzymes include thermostable enzymes, e.g. thermostable pullulanases as disclosed in PCT Publ. No. WO 92/02614, published Feb. 20, 1992, the disclosure of which is incorporated by reference, and which are obtained from members of the genus Pyrococcus. The debranching enzyme may be in solution during debranching or it may be immobilized on a solid support.

The debranching enzyme preparation should be as specific as possible for the hydrolysis of the 1,6-glucosidic bond of amylopectin and amylose. Thus, the enzyme preparation, if it contains a mixture of enzymes, is preferably essentially free of enzymes capable of hydrolyzing α-1,4-glucosidic bonds. Minimizing hydrolysis of α-1,4-glucosidic bonds will help to minimize the amounts of dextrose and soluble oligomers produced during debranching. Because these soluble saccharities are not believed to contribute to the functionality of the debranched material, minimizing their production will enhance the yield of functional material.

The debranching enzyme is allowed to act upon the solubilized starch containing amylopectin. The optimum concentration of enzyme and substrate in the debranching medium will, in general, depend upon the level of activity of the enzyme which, in turn, will vary depending upon the enzyme source, enzyme supplier, and the concentration of the enzyme in commercial batches. When the isoamylase E.C. 3.2.1.68, derived from *Pseudomonas amyloderamosa,* available from Sigma Chemical Co., St. Louis, Mo., is employed, typical conditions include the treatment of a starch solution at 5% to 30% by weight starch solids with about 50 units of enzyme, per gram of starch, for a period of about 48 hours to obtain substantially complete debranching.

The optimum pH and temperature of the debranching medium will also depend upon the choice of enzyme. The debranching medium may, in addition to the water used to solubilize the starch, contain buffers to ensure that the pH will be maintained at an optimum level throughout the debranching. Examples of useful buffers include acetates, citrates, and the salts of other weak acids. With the isoamylase described above, the pH is preferably maintained at about 4.0 to 5.0 and the temperature from about 40° C. to about 50° C. With the thermostable pullulanase described above, the pH is preferably maintained between 5 and 7 and the optimum temperature should be between 85° C. and 115° C.

The debranching is allowed to proceed until the desired degree of debranching has been obtained. The precise degree of debranching needed to obtain the desired particle gel of the debranched amylopectin starch may vary depending upon the source of the starch and the precise properties desired in the resulting gel. Preferably, the degree of debranching is sufficient to convert more than about 80% of the amylopectin in the starch to short chain amylose and, more preferably, at least about 90% of the amylopectin.

In preferred embodiments, essentially all of the amylopectin is converted to short chain amylose. The amount of short chain amylose can be measured by gel permeation chromatography as set forth in U.S. Pat. No. 4,971,723, wherein short chain amylose is calculated from the relative area of the peak obtained within the molecular weight range of 500 to 20,000. Thus, preferably less than 20% of the amylopectin that was originally present will be present as molecular species having a molecular weight in excess of 20,000 g/mol, and most preferably, essentially no amylopectin having a molecular weight in excess of 20,000 g/mol will remain. (It should be noted that if amylose is present, at least a portion thereof may be debranched to produce molecules above the 20,000 g/mol cut-off and molecules below the 20,000 g/mol cut-off. To measure how much of the material eluting between 500 g/mol and 20,000 g/mol is debranched amylopectin and how much is debranched amylose, it may be necessary to fractionate the starting starch into its amylose and amylopectin fractions and then debranch and elute each fraction separately.)

The solution of debranched starch may also be treated to remove impurities therefrom. Treatment with, for example, activated carbon will remove residual proteins and lipids that may contribute to off-flavors and/or colors.

The solution of gelatinized, and optionally debranched, starch is then allowed to form a precipitate of retrograded starch. Generally, the solution will be cooled from the temperature at which the starch is pasted to reduce the solubility of the gelatinized starch therein. The solution will typically be held at elevated temperature (e.g. 65° C. to 90° C.) until substantial equilibrium is achieved between the supernatant and the precipitate. The precipitate can be isolated from the supernatant, e.g. by centrifugation, prior to fragmentation, but isolation from the supernatant is not necessary to form a useful product.

Heating (e.g. to about 70° C.) of the particles while in contact with the aqueous medium to dissolve at least a portion of the mass of the particles and then cooling of the suspension/solution can also be employed in forming the particle gel of this invention. This heating to an elevated temperature and then reformation of the particles tends to make the particles resistant to melting or dissolving when an aqueous dispersion of the particles is exposed to heat in processing, e.g. in a pasteurization step. In general, the higher the temperature to which the particles in the liquid medium are heated (and thus the greater the amount of precipitate that is redissolved), the higher the temperature at which the resulting aqueous dispersion of the particles will be stable. Repetition of the dissolving and reformation may improve the temperature stability of the resulting aqueous dispersion.

It is also advantageous to heat the precipitate to redissolve a substantial portion of the low melting polysaccharides and then treat the heated suspension of precipitate with acid or enzyme to hydrolyze soluble polysaccharides in the solution. (It may also be advantageous to filter the slurry while hot to remove soluble polysaccharides or their hydrolysates.) The dissolving and reprecipitation steps alone improve the stability of the aqueous dispersion by increasing the amount of the fragmented precipitate which remains as insoluble fragments in an aqueous dispersion that is exposed to heat. Further, a slow rate of heating and/or cooling (e.g. from about 0.005° C./min. to about 0.5° C./min. for each) may be advantageous. However, the remaining soluble fraction of the precipitate can associate to form relatively large particles that are present in the precipitate after fragmentation and that can contribute a "chalky" or "gritty" texture to the dispersion. Treatment of the heated suspension/solution of the precipitate with acid or enzyme to hydrolyze a substantial portion of the soluble fraction can reduce or eliminate such large particles. Typical treatment conditions will involve mild hydrolysis catalyzed by acid, e.g. in a solution of 0.1 N HCl for one hour, or, preferably, by enzyme, e.g. α-amylase.

The precipitated amylose is then hydrolyzed with an acid (e.g. a mineral acid such as hydrochloric acid or sulfuric acid) or treated with an α-amylase enzyme, i.e. an endo-enzyme capable of hydrolyzing the 1,4-glucosidic bond of amylose and amylopectin to yield products having an α configuration. The acid or enzyme is allowed to act upon the precipitated amylose and thereby hydrolyze those regions in the precipitate that are susceptible to hydrolysis. The optimum concentration of acid or enzyme and substrate in the hydrolysis medium will, in general, depend upon the level of activity of the acid enzyme which, in turn, will vary depending upon the acid strength or enzyme source, enzyme supplier and the concentration of the enzyme in commercial batches. Typical treatment conditions will involve mild hydrolysis catalyzed by acid, e.g. in a solution of 0.1 N HCl for one hour, or, preferably, by enzyme, e.g. α-amylase.

The α-amylase can be from a variety of sources. Common sources of α-amylase are bacterial, e.g. *Bacillus subtilis*, or fungal, e.g. *Aspergillus oryzae*, or mammalian, e.g. human salivary, porcine pancreatic, etc. The optimum pH and temperature of the hydrolysis medium will also depend upon the choice of enzyme. The hydrolysis medium may, in addition to the water used in the hydrolysis of the starch, contain buffers to ensure that the pH will be maintained at an optimum level throughout the hydrolysis. Examples of useful buffers include acetates, citrates, phosphates, and the salts of other weak acids. With porcine pancreatic α-amylase, the pH is preferably maintained at about 6.0 to 8.0 and the temperature from about 20° C. to about 30° C.

The hydrolysis is allowed to proceed until the desired degree of hydrolysis has been obtained. The precise degree of hydrolysis needed to obtain the desired particle gel of the fragmented amylose starch may vary depending upon the source of the starch and the precise properties desired in the resulting gel. Typically, the degree of hydrolysis will be such that fragmentation of the product will yield a gel that exhibits a transition from a region of substantially constant dynamic elastic modulus (G') versus shear strain to a region of decreasing G' versus shear strain, said transition being at a shear strain of less than about 50 millistrain, and preferably less than about 10 millistrain. The transition indicates fracture of the particle network within the particle gel and is typically a sharp transition. The dynamic elastic modulus can be measured with a Bohlin model VOR Rheometer, from Bohlin Rheologi, Inc., East Brunswick, N.J.

The hydrolysis medium is essentially aqueous. Generally, it will contain no more than a trace, if any, of organic solvents (e.g. ethanol). Organic solvents may react with the saccharide by-products (e.g. dextrose to form at least traces of ethyl glucoside), may otherwise affect the hydrolysis reaction (e.g. solvent effects) and/or may contaminate the starch hydrolysate product.

The progress of the hydrolysis may be followed by taking small samples of slurry from an in-progress batch of the starch hydrolysate, adjusting the pH of the slurry (e.g. to 4-5), isolating the solid starch hydrolysate residue from the slurry sample, and mechanically disintegrating the residue under the conditions intended for the batch as a whole. The yield stress of a 20% aqueous dispersion can then be measured to determine if the acid-hydrolysis has progressed to a desired degree (typically from about 100 pascals to about 3,000 pascals, preferably at least about 300 pascals). Also, samples of insoluble residue can be isolated for a determination of peak molecular weight (or weight average molecular weight) by gel permeation chromatography or of supernatant for dextrose content and the results used as a measure of the degree of hydrolysis; both molecular weight (particularly $M_w$) and dextrose content should correlate well with yield stress of the resulting starch hydrolysate upon fragmentation for a given set of reaction conditions (i.e. acid concentration, starch solids concentration, and hydrolysis time and temperature).

After the desired degree of hydrolysis is obtained, the acid is neutralized or the α-amylase enzyme in solution is deactivated, e.g. by heating to denature the enzyme. The hydrolysis medium may be concentrated by removal of water therefrom, e.g. by evaporation, to facilitate precipitation.

If the amylose starch chosen as a starting material is relatively low in amylose content, e.g. less than 40% amylose, it may be useful to stage the hydrolysis reaction. This staging will involve an initial hydrolysis period at less than 70° C., e.g. at 60°, for a time sufficient to hydrolyze and leach from the retrograded material a significant amount of amorphous and low melting starch. The initial hydrolysis period is then followed by a second hydrolysis period during which the temperature of the reaction slurry is maintained above 70° C., preferably above 90° C. The starch hydrolysate from the initial period can be isolated from the reaction slurry and then reslurried for the second hydrolysis period, but there is no need for such isolation between the stages.

As an alternative to hydrolysis at above 90° C., the starch can be hydrolyzed at temperatures below 70° C. and then heated, in aqueous slurry at a substantially neutral pH, to a temperature above 90° C. for a time sufficient to raise the melting onset temperature to at least 90° C. when measured at 20% starch hydrolysate solids. The starch hydrolysate can be isolated from the reaction slurry and reslurried for such treatment or the reaction slurry, after neutralization, can simply be heated above 90° C. Such heat treatment will typically involve holding a slurry comprised of a major amount of water and a minor amount of starch hydrolysate at a substantially neutral pH, e.g. a pH of about 3-8, preferably about 4-7, and at a temperature between about 90° C. and about 130° C. for about ½ hour to about 3 hours. The resulting starch hydrolysate can then be isolated as described more fully below.

The starch hydrolysis product of the slurry is isolated as the solid phase residue by separation thereof from the aqueous phase of the slurry. Techniques for such isolation include filtration (e.g. horizontal belt filtering), centrifugation (e.g. disk, decanter or solid bowl), sedimentation, and other suitable dewatering operations. It is advantageous to maintain the slurry at an elevated temperature (e.g. 90° to 130° C.) during isolation to keep the undesirable saccharides in solution. It should be noted that a solid bowl centrifuge has been found to be one of two most practical means of isolating the solid phase residue by sedimentation.

The principles and modes of operation of imperforate bowl centrifuges are described by A. C. Lavanchy and F. W. Keith, "Centrifugal Separation", *Encyclopedia of Chemical Technology*, Vol. 5, pp. 194–233 (Kirk-Othmer, eds., John Wiley & Sons, Inc., New York, N.Y., 3d ed., 1979) and P. A. Schweitzer, *Handbook of Separation Techniques for Chemical Engineers*, pp. 4–60 to 4–88 (McGraw Hill, New York, N.Y., 1988), the disclosures of each of which are incorporated herein. (It should be noted that Schweitzer uses the term "Solid-Wall Basket Centrifuge".)

It has been found that microfiltration is an effective means of separating an insoluble starch hydrolysate residue from an aqueous slurry thereof which also contains a relatively large amount of dissolved species, e.g. salt and saccharides. Microfiltration is described generally in D. R. Paul and G. Morel, "Membrane Technology", *Encyclopedia of Chemical Technology*, Vol. 15, pp. 92–131 (Kirk-Othmer, eds., John Wiley & Sons, Inc., New York, N.Y., 3d ed., 1981), the disclosure of which is incorporated herein by reference.

Typically, a liquid including small dissolved molecules is forced through a porous membrane. Large dissolved molecules, colloids and suspended solids that cannot pass through the pores are retained. Components retained by the membrane are collectively referred to as a concentrate or retentate. Components which traverse the membrane are referred to collectively as filtrate or permeate. Diafiltration is a microfiltration process in which the retentate is further purified or the permeable solids are extracted further by the addition of water to the retentate. This process is analagous to washing of a conventional filter cake. The use of microfiltration removes salts formed by the neutralization of the alkaline solution and other molecular species small enough to pass through the membrane.

Ultrafiltration is generally described and discussed by P. R. Klinkowski, "Ultrafiltration", *Encyclopedia of Chemical Technology*, Vol. 23, pp. 439–461 (Kirk-Othmer, eds., John Wiley & Sons, New York, N.Y., 3d ed., 1983), the disclosure of which is incorporated by reference herein. Ultrafiltration is a pressure-driven filtration on a molecular scale. The porous membrane typically has a pore size ranging from 0.005 to 20 micrometers (or microns). While a distinction is often made in the separation art between ultrafiltration (pore size range of 2 to 20 nanometers) and microfiltration (pore size greater than 20 nanometers), the terms will be used interchangeably herein unless expressly noted otherwise.

The acid in the slurry can be neutralized either before or after isolation of the hydrolysate. Any food grade alkali (e.g. sodium hydroxide, soda ash, potassium hydroxide, etc.) can be used to neutralize the slurry, preferably to a pH of from about 4 to about 5. However, it may be advantageous (in terms of obtaining a desirably bland flavor for the hydrolysate) to (i) only partially neutralize the slurry to a weakly acidic pH (e.g. from about 2.0 to about 3.5) and (ii) then hold the slurry at a moderately elevated temperature (e.g. 25° C. to 75° C.) for a short period of time (e.g. 15 minutes to 24 hours), prior to isolation, followed by washing and then neutralization of the solid hydrolysate residue to a substantially neutral pH (e.g. about 4.5 to about 5.0). This acid washing of the starch hydrolysate is particularly advantageous when employed in the context of microfiltration of the starch hydrolysate slurry Using a ceramic microfiltration membrane contained within an acid resistant (e.g. polyvinyl chloride) housing.

By "microporous ceramic membrane" is meant any ceramic layer (including "supported layer articles") having micropores and sufficient structural integrity to withstand the pressure needed to isolate the insoluble starch hydrolysate residue from the liquid phase of the aqueous slurry over a desired period of time (e.g. from 15 minutes to 24 hours). It is believed that the high pressure used to isolate the insoluble starch hydrolysate residue creates turbulent flow at the membrane's surface which prevents small particles in the slurry from "blinding off" the pores of the membrane (as has been observed with conventional filtration equipment as discussed below).

A typical microporous ceramic membrane is comprised of a microporous ceramic article having at least one macroscopic passage therethrough (typically a cylindrical article having cylindrical passages) substantially parallel to the axis of symmetry of the cylindrical article. While the article may be "microporous" itself, the ceramic cylinder may act principally as a support (i.e. in a "supported layer article") for a microporous layer (or layers with regard to multi-passage articles) which covers the surfaces defined by the passages through the ceramic article. The porosity of the ceramic article, and any microporous layer associated therewith as described above, can be varied as desired, with the pore size of any such layer being smaller than that of the article. In typical operation, such a ceramic filter element (i.e. cylindrical and microporous ceramic article) is contained in hollow cylindrical housing and slurry is fed into the passages under pressure through a feed manifold that prevents leakage into the housing. The exit of the isolated starch hydrolysate residue from the passages at the other end of the ceramic filter element is controlled by an exit manifold which also prevents leakage into the housing where the filtrate or permeate is contained. Ceramic filter elements and their use are described in "Solve Tough Process Filtration Problems with Ceraflo Ceramic Systems", a technical bulletin, Lit. No. SD113, 2/89 89–418, published (1989) by Millipore Corporation, Bedford, Mass., the disclosure of which is incorporated by reference.

The isolated amylose hydrolysate is typically dried (e.g. to a low moisture content, typically 3–12%) after isolation to allow for handling and storage prior to further processing. Examples of drying techniques include spray drying, flash drying, tray drying, belt drying, and sonic drying. The dried hydrolysate may be hygroscopic. Thus, some rehydration during handling and storage may occur. Depending upon the precise composition of the hydrolysate and the conditions (including length of time) of storage, steps to maintain the moisture at a low content may be necessary (e.g. moisture barrier packaging and/or control of humidity in the storage environment). If the moisture content is allowed to rise too far (e.g. greater than about 20%, or possibly greater than 15%), bulk handling problems and/or microbiological stability problems might arise.

The retrograded, hydrolyzed, and heat-treated amylose starch is subjected to a physical fragmentation as by mechanical disintegration, i.e. fragmented. The degree of fragmentation will be sufficient to cause the material to form a particle gel in an aqueous medium. The mechanical disintegration of the hydrolysate may be carried out in several ways, as by subjecting it to attrition in a mill, or to a high speed shearing action, or to the action of high pressures. Disintegration is generally carried out in the presence of a major amount by weight of a liquid medium, preferably water. Although tap water is the preferred liquid medium for the dispersion of fragmented amylose starch hydrolysate, other liquids are suitable provided sufficient water is present to hydrate the fragmented amylose starch hydrolysate and, thus, result in a dispersion having the characteristics of a particle gel. Sugar solutions, polyols, of which glycerol is an example, alcohols, particularly ethanol, isopropanol, and the like, are good examples of suitable liquids that can be in admixture with water in the liquid medium. Typically, however, the amylose starch hydrolysate will be physically fragmented in potable water.

The mechanical disintegration is preferably accomplished by subjecting an aqueous dispersion of the hydrolysate to high shear, e.g. in a Waring blender or a homogenizer such as that disclosed in U.S. Pat. No. 4,533,254 (Cook et al.) and commercially available as a MICROFLUIDIZER TM from Microfluidics Corporation, Newton, Mass., or a homogenizer such as the RANNIE TM high pressure laboratory homogenizer, Model Mini-lab, type 8.30 H, APV Rannie, Minneapolis, Minn. Homogenizers useful in forming suspensions or emulsions are described generally by H. Reuter, "Homogenization", *Encyclopedia of Food Science*, pp. 374–376, (M. S. Peterson and A. H. Johnson, eds., AVI Publ. Co., Westport, Conn., 1978), L. H. Rees and W. D. Pandolfe, "Homogenizers", *Encyclopedia of Food Engineering*, pp. 467–472 (C. W. Hall et al., eds., AVI Publ. Co., Westport, Conn., 1986), and W. C. Griffin, "Emulsions", *Encyclopedia of Chemical Technology*, Vol. 8, pp. 900–930 (Kirk-Othmer, eds., John Wiley & Sons, Inc., New York, N.Y., 3d ed., 1979), the disclosures of which are incorporated herein by reference.

The temperature of the amylose starch hydrolysate during the fragmentation step should be maintained below the temperature at which a major portion of the hydrolysate will dissolve in the aqueous medium. However, the heat treatment to remove water-soluble hydrolysate material should make the remaining retrograded material relatively insensitive to elevated temperatures. Thus, it will probably not be necessary to cool the material during disintegration. Whatever method is used, the disintegration is carried out to such an extent that the resulting finely-divided product is characterized by its ability to form a particle gel in the liquid medium in which it is attrited or in which it is subsequently dispersed.

The amylose starch hydrolysate particles which make up the particle gel can be analyzed in a variety of ways. Rheological measurements can be made to determine the theological characteristics of the resulting dispersion. Typically, the aqueous dispersion of amylose starch hydrolysate particles will exhibit a transition in dynamic elastic modulus (G') versus shear strain at less than about 50 millistrain, and preferably less than about 10 millistrain, said transition being from a substantially constant G' versus shear strain to a decreasing G' versus shear strain. The transition indicates fracture of the particle network within the particle gel and is typically a sharp transition.

It should also be noted that mechanical disintegration may be sufficient to produce an aqueous dispersion having the desired particle gel characteristics, but still leave a sufficient number of particles of sufficient size to exhibit a "particulate" or "chalky" mouthfeel when ingested. Such chalkiness can be reduced by the mild hydrolysis discussed above or by reducing the particle size of the starch hydrolysate before, during or after mechanical disintegration so that substantially all (typically at least about 95%, preferably at least 99%) of the hydrolysate will pass a U.S. #325 mesh sieve (i.e. substantially all particles are less than 45 microns). An example of a milling device suitable for such size reduction is a TROST TM Air Impact Mill from Gatlock, Inc., Newton, Pa.

The use of the retrograded, hydrolyzed, heat-treated and fragmented, amylose starch hydrolysate allows for the replacement of a substantial portion (e.g. from 10% to 100% by weight) of the fat and/or oil in a food formulation. The precise level of replacement that is possible without significantly decreasing the organoleptic quality of the food will generally vary with the type of food. For example, in a French-style salad dressing, it is generally possible to completely replace the oil component that is normally present. In other types of foods, e.g. frostings, icings, cream fillings, ice cream, margarine, etc., a major amount of the fat and/or oil (e.g. about 50% to about 80%) can be replaced with little effect on the organoleptic desirability of the food. Examples of typical foods in which fat and/or oil can be replaced include frostings (e.g. icings, glazes, etc.), creme fillings, frozen desserts (e.g. ice milk, sherbets, etc.), dressings (e.g. pourable or spoonable salad and/or sandwich dressings), meat products (e.g. sausages, processed meats, etc.), cheese products (e.g. cheese spreads, processed cheese foods), margarine, fruit butters, other imitation dairy products, puddings (e.g. mousse desserts), candy (e.g. chocolates, nougats, etc.), and sauces, toppings, syrups and so on.

Generally, it will be desirable to remove sufficient fat from a given food formulation to achieve a reduction in calories of at least one-third per customary serving or make a label claim of "cholesterol-free". (In this regard, see, for example, the list of standard serving sizes for various foods published in Food Labelling; Serving Sizes, 55 Fed. Reg. 29517 (1990) (to be codified at 21 C.F.R. 101.12), the disclosure of which is incorporated herein by reference, and the restrictions on labeling "cholesterol-free" at Food Labelling; Definitions of the Terms Cholesterol Free, Low Cholesterol and Reduced Cholesterol, 55 Fed. Reg. 29456 (1990)). It should also be noted that the fat removed from a particular formulation may be replaced with an equal amount by weight of an aqueous dispersion of fragmented amylose starch hydrolysate, but that such equality may not be necessary or desirable in all instances. Further, it may be desirable to remove fat and add another ingredient (e.g. a gum, polydextrose, a protein, etc.) along with the aqueous dispersion of starch hydrolysate.

While this invention is generally directed to the replacement of fat and/or oil in a food formulation, it is of course within the contemplation of this invention that a fragmented, amylose starch hydrolysate will be used in an entirely new formulation to which it contributes fat-like organoleptic qualities but is not, in the strictest sense, replacing a pre-existing fat or oil ingredient. Moreover, it is contemplated that the fragmented amylose starch hydrolysate will have utility as a thickener, bodying agent, or the like in foods that normally do not have a significant fat or oil component.

In general, the fragmented amylose starch hydrolysate will be incorporated into the food as an aqueous dispersion, typically comprised of a major amount (i.e. greater than 50% by weight) of water or other liquid medium and a minor amount (i.e. less than 50% by weight, typically 10% to 40%) of amylose starch hydrolysate solids. Alternatively, the isolated amylose starch hydrolysate can be mixed with the food along with water and then subjected to disintegration in those instances when the other ingredients of the food are capable of withstanding the condition of disintegration, e.g. a salad dressing or imitation sour cream.

It is contemplated that commercial production and use may involve hydrolysis, mechanical disintegration, and drying (e.g. spray drying) of the fragmented starch hydrolysate to produce an item of commerce. This item of commerce will then be purchased by a food processor for use as an ingredient. To incorporate the dried, fragmented, amylose starch hydrolysate into a food product, it may be useful and/or necessary to further mechanically disintegrate the starch hydrolysate while dispersing it into the foodstuff in which it will be employed. However, the techniques employed for such mechanical disintegration should not need to be nearly as vigorous as the original mechanical disintegration prior to drying.

As noted above, the terms "food" and "foodstuffs" are intended broadly, as relating to both nutritional and/or functional food ingredients. It is contemplated that one or more food ingredients may be mixed with the aqueous dispersion of fragmented amylose starch hydrolysate, or even dry mixed with the hydrolysate prior to mechanical disintegration.

Among the food ingredients which may be included in the food formulations of this invention are flavors, thickeners (e.g. starches and hydrophilic colloids), nutrients (e.g. carbohydrates, proteins, lipids, etc.), antioxidants, antimicrobial agents, non-fat milk solids, egg solids, acidulants, and so on.

Hydrophilic colloids can include natural gum material such as xanthan gum, gum tragacanth, locust bean gum, guar gum, elgin, elginares, gelatin, Irish moss, pectin, gum arabic, gum ghatti, gum karaya and plant hemicelluloses, e.g. corn hull gum. Synthetic gums such as water-soluble salts of carboxymethyl cellulose can also be used. Starches can also be added to the food. Examples of suitable starches include corn, waxy maize, wheat, rice, potato, and tapioca starches.

Non-fat milk solids which can be used in the compositions of this invention are the solids of skim milk and include proteins, mineral matter and milk sugar. Other proteins such as casein, sodium caseinate, calcium caseinate, modified casein, sweet dairy whey, modified whey, and whey protein concentrate can also be used herein.

For many foods, it is accepted practice for the user to add the required amount of eggs in the course of preparation and this practice may be followed just as well herein. If desired, however, the inclusion of egg solids, in particular, egg albumen and dried yolk, in the food are allowable alternatives. Soy isolates may also be used herein in place of the egg albumen.

Dry or liquid flavoring agents may be added to the formulation. These include cocoa, vanilla, chocolate, coconut, peppermint, pineapple, cherry, nuts, spices, salts, flavor enhancers, among others.

Acidulants commonly added to foods include lactic acid, citric acid, tartaric acid, malic acid, acetic acid, phosphoric acid, and hydrochloric acid.

Generally, the other components of the various types of food formulations will be conventional, although precise amounts of individual components and the presence of some of the conventional components may well be unconventional in a given formulation. For example, the conventional other components for foods such as frozen desserts and dressings, are described in European Patent Publication No. 0 340 035, published Nov. 2, 1989 (the pertinent disclosure of which is incorporated herein by reference), and the components and processing of table spreads is disclosed in Lowery U.S. Pat. No. 4,869,919, the disclosure of which is incorporated by reference.

A particularly advantageous use of the fragmented starch hydrolysates described herein may be the use thereof to replace a portion of the shortening used in a layered pastry article. In layered pastry articles (Danish, croissants, etc.), layers of a bread dough are assembled with a "roll-in" placed between the layers. The roll-in commonly contains a "shortening" (i.e. a fat and/or oil component) from an animal (e.g. butter) or vegetable (e.g. partially hydrogenated soybean oil) source. The assembled article, optionally containing a filling or topping, is then baked to form a finished pastry. At least a portion of the shortening of an otherwise conventional roll-in can be replaced with an aqueous dispersion of fragmented, amylose hydrolysate, preferably in admixture with an emulsifier (e.g. mono- and/or di-glycerides), and used to make a layered pastry.

The following examples will illustrate the invention and variations thereof within the scope and spirit of the invention will be apparent therefrom. All parts, percentages, ratios and the like are by weight throughout this specification and the appended claims, unless otherwise noted in context.

EXAMPLES

EXAMPLE 1

High amylose starch (HI-SET C, National Starch and Chemical Co.) was first solubilized at 7% dry solids by weight by heating a slurry thereof in water in a pressure vessel to about 150° C. The resulting solution was cooled to room temperature (about 25° C.) and allowed to stir for 20 hours during which time a thick mass of crystals precipitated. Acid (HCl in an amount of 0.45–0.46 meq/gm of slurry) was added and hydrolysis of the crystals in the slurry was carried out at 70° C. for the time indicated below. The insoluble product was isolated by centrifugation with a water wash (at room temperature) to remove low molecular weight solubles. The results of two separate replicates hydrolyzed for different time periods are shown below, where Mw is weight average molecular weight by gel permeation chromatography. All values in the table below can be determined as in PCT Publication No. WO 91/12728, published Sep. 5, 1991.

| Time | Mw | Insolubles (wt %) | Yield Stress (Pas) |
| --- | --- | --- | --- |
| 6 hr | 8,581 | 22.1 | 910 |
| 4 hr | 10,203 | 32.6 | 1165 |

The products were fragmented at 20% dry starch hydrolysate solids at 8,000 psi in a Microfluidizer homogenizer at 60° C. The DSC endotherm of the 6 hour product was very broad beginning at about 80° C. and ending at about 138° C. This endotherm appeared to consist of two domains which peak at about 100° C. and about 115° C., respectively. The material in the higher temperature domain can be isolated by washing the the material with water in a pressurized vessel at a temperature above 100° C., e.g. from about 105° C. to about 110° C.

EXAMPLE 2

High amylose starch (HI-SET C, National Starch and Chemical Co.) was first solubilized at 8.0% dry solids by weight by heating a slurry thereof in water in a pressure vessel to about 162° C. The resulting solution was cooled to room temperature (about 25° C.) and allowed to stir for 20 hours during which time a thick mass of crystals precipitated. Acid (HCl in an amount of 0.44 meq/gm of slurry) was added and hydrolysis of the crystals in the slurry was carried out at 69° C. for four hours after which the solution was neutralized to pH 4.3 with 1.5N sodium hydroxide. The insoluble product was isolated by microfiltration of the slurry while the slurry was held at 94° to 95.8° C. The DSC endotherm of the resulting product appeared to consist of of a single domain which peaked at about 120° C.

What is claimed is:

1. A method of preparing a heat-treated and fragmented amylose starch hydrolysate comprising:
   gelatinizing and retrograding an amylose starch in the presence of an aqueous medium to prepare an aqueous slurry of retrograded amylose;
   hydrolyzing said retrograded amylose to a degree sufficient to permit physical fragmentation to form a particle gel comprised of a minor amount of said retrograded amylose in a major amount of an aqueous medium;
   physically separating said hydrolyzed and retrograded amylose from an aqueous medium at an elevated temperature to remove a water-soluble hydrolysate fraction with said aqueous medium to produce a hydrolyzed and retrograded amylose essentially free of water-soluble hydrolysate products; and
   physically fragmenting by mechanical disintegration a minor amount of said hydrolyzed and retrograded amylose free of water-soluble hydrolysate products in a major amount of an aqueous medium to produce a particle gel thereof.

2. A method of claim 1 wherein said elevated temperature is greater than about 90° C.

3. A method of claim 1 wherein said particle gel exhibits a transition in dynamic elastic modulus versus shear strain from substantially constant dynamic elastic modulus to decreasing dynamic elastic modulus, said transition being exhibited at a shear strain of less than about 50 millistrain.

4. A method of claim 1 wherein said starch is derived from starch from a variety of Zea mays.

5. A method of claim 1 wherein said starch is derived from a starch having at least about 40% by weight amylose.

6. A method of claim 1 wherein said retrograded, hydrolyzed, heat-treated, and fragmented, amylose starch has only a minor amount of 90° C. water solubles.

7. A foodstuff having a reduced level of fat and/or oil comprising a mixture of a foodstuff and a particle gel as a replacement for at least a substantial portion of the fat and/or oil of said foodstuff, said particle gel comprising a minor amount of a retrograded, hydrolyzed, heat-treated, and fragmented by mechanical disintegration, amylose starch and a major amount of an aqueous liquid.

8. A foodstuff of claim 7 wherein said particle gel exhibits a transition in dynamic elastic modulus versus shear strain from substantially constant dynamic elastic modulus to decreasing dynamic elastic modulus, said transition being exhibited at a shear strain of less than about 50 millistrain.

9. A foodstuff of claim 7 wherein said starch is derived from starch from a variety of Zea mays.

10. A foodstuff of claim 7 wherein said starch is derived from a starch having at least about 40% by weight amylose.

11. A foodstuff of claim 7 wherein said retrograded, hydrolyzed, heat-treated, and fragmented, amylose starch has only a minor amount of 90° C. water solubles.

12. A method of formulating a food containing a fat and/or oil ingredient comprising replacing at least a substantial portion of said fat and/or oil ingredient with a particle gel, said particle gel comprising a minor amount of a retrograded, hydrolyzed, heat-treated, and fragmented by mechanical disintegration, amylose starch and a major amount of an aqueous liquid.

13. A method of claim 12 wherein said particle gel exhibits a transition in dynamic elastic modulus versus shear strain from substantially constant dynamic elastic modulus to decreasing dynamic elastic modulus, said transition being exhibited at a shear strain of less than about 50 millistrain.

14. A method of claim 12 wherein said starch is derived from starch from a variety of Zea mays.

15. A method of claim 12 wherein said starch is derived from a starch having at least about 40% by weight amylose.

16. A method of claim 12 wherein said retrograded, hydrolyzed, heat-treated, and fragmented, amylose starch has only a minor amount of 90° C. water solubles.

17. An aqueous dispersion useful as a replacement for fats and/or oils comprising a major amount by weight of water and a minor amount of weight of a retrograded, hydrolyzed, heat-treated, and fragmented by mechanical disintegration, amylose starch, the degree of hydrolysis and fragmentation of said starch being sufficient to form a particle gel of said dispersion.

18. An aqueous dispersion of claim 17 wherein said particle gel exhibits a transition in dynamic elastic modulus versus shear strain from substantially constant dynamic elastic modulus to decreasing dynamic elastic modulus, said transition being exhibited at a shear strain of less than about 50 millistrain.

19. An aqueous dispersion of claim 17 wherein said starch is derived from starch from a variety of Zea mays.

20. An aqueous dispersion of claim 17 wherein said starch is derived from a starch having at least about 40% by weight amylose.

21. An aqueous dispersion of claim 17 wherein said retrograded, hydrolyzed, heat-treated, and fragmented, amylose starch has only a minor amount of 90° C. water solubles.

* * * * *